United States Patent
Bannwart

(10) Patent No.: US 11,486,382 B2
(45) Date of Patent: Nov. 1, 2022

(54) DEVICE WITH A PERISTALTIC PUMP UNIT WHICH CAN BE COUPLED

(71) Applicant: MEDELA HOLDING AG, Baar (CH)

(72) Inventor: Lukas Bannwart, Rotkreuz (CH)

(73) Assignee: MEDELA HOLDING AG, Baar (CH)

( * ) Notice: Subject to any disclaimer, the term of this patent is extended or adjusted under 35 U.S.C. 154(b) by 270 days.

(21) Appl. No.: 16/489,992

(22) PCT Filed: Mar. 16, 2018

(86) PCT No.: PCT/EP2018/056705
§ 371 (c)(1),
(2) Date: Aug. 29, 2019

(87) PCT Pub. No.: WO2018/172217
PCT Pub. Date: Sep. 27, 2018

(65) Prior Publication Data
US 2020/0011321 A1    Jan. 9, 2020

(30) Foreign Application Priority Data

Mar. 23, 2017 (EP) ..................................... 17162577

(51) Int. Cl.
*F04B 43/12* (2006.01)
*A61M 1/00* (2006.01)

(52) U.S. Cl.
CPC ....... *F04B 43/1276* (2013.01); *A61M 1/0001* (2013.01); *A61M 1/0058* (2013.01);
(Continued)

(58) Field of Classification Search
CPC .. F04B 43/1276; F04B 43/12; F04B 43/1207; F04B 43/1215; F04B 43/1223;
(Continued)

(56) References Cited

U.S. PATENT DOCUMENTS

| | | |
|---|---|---|
| 4,181,476 A | 1/1980 | Malbec |
| 4,218,197 A | 8/1980 | Meyer et al. |
| (Continued) | | |

FOREIGN PATENT DOCUMENTS

| | | |
|---|---|---|
| CN | 102844059 A | 12/2012 |
| CN | 205117687 U | 3/2016 |
| (Continued) | | |

OTHER PUBLICATIONS

Malbec , Peristaltic and especially monosatellite pump, 1991, Google Patents Translation (Year: 1991).*

(Continued)

*Primary Examiner* — Quang D Thanh
*Assistant Examiner* — Brandon W. Levy
(74) *Attorney, Agent, or Firm* — Marshall, Gerstein & Borun LLP

(57) ABSTRACT

A device for supplying and/or aspirating a fluid substance to or from a human or animal body is provided, which device has a drive unit with a drive, an attachment part, and coupling element. The attachment part has a peristaltic pump unit with a pump head having roller elements which are movable freely and independently of one another and serve for rolling on a hose. The coupling element serves to transmit a movement from the drive to the pump head. The pump head has a decoupled state in which the roller elements apply no or a comparatively low mechanical pressure to the hose, and a coupled state in which the roller elements are pressed by the coupling element against the hose with a comparatively high mechanical pressure.

10 Claims, 7 Drawing Sheets

(52) U.S. Cl.
CPC ............ *A61M 1/80* (2021.05); *A61M 2202/08* (2013.01); *A61M 2205/12* (2013.01)

(58) Field of Classification Search
CPC .......................... F04B 43/123; F04B 43/1238; F04B 43/1246; F04B 43/1253; F04B 43/1261; F04B 43/1269; F04B 43/1284; F04B 43/1292; F04B 43/14; F04B 45/08; F04B 43/0072; F04B 43/00; F04B 23/06; A61M 2202/08; A61M 2205/12; A61M 1/80; A61M 1/0001; A61M 1/0058; A61M 1/77; A61M 1/92; A61M 1/60; A61M 1/64; A61M 1/65; A61M 1/66; A61M 1/68; A61M 1/682; A61M 1/684; A61M 1/98; A61M 1/982; A61M 1/984; A61M 1/985; A61M 1/802; A61M 1/804; A61M 1/81; A61M 1/815; A61M 1/82; A61M 5/14232; A61M 2210/0612; A61M 3/0258; A61M 2205/121; A61M 5/14216; A61M 1/0023; A61M 1/90; A61M 2205/128; A61M 1/72; A61M 1/74; A16M 1/902; B01L 2300/123; B67D 1/108

See application file for complete search history.

(56) References Cited

U.S. PATENT DOCUMENTS

| | | |
|---|---|---|
| 5,044,902 A | 9/1991 | Malbec |
| 5,655,897 A | 8/1997 | Neftel et al. |
| 5,927,956 A | 7/1999 | Lim et al. |
| 6,685,450 B2 * | 2/2004 | Bandis ............... F04B 43/1284 417/477.6 |
| 9,511,186 B1 * | 12/2016 | Nystrom ................. F04C 18/22 |
| 2005/0129545 A1 * | 6/2005 | Prosek, Jr. .......... F04B 43/1253 417/474 |
| 2008/0038128 A1 * | 2/2008 | Haar ..................... F04B 43/082 417/474 |
| 2013/0071270 A1 | 3/2013 | Zupp et al. |
| 2014/0163487 A1 | 6/2014 | Tout et al. |
| 2016/0123320 A1 * | 5/2016 | Tsoukalis .......... A61M 5/14232 417/477.2 |

FOREIGN PATENT DOCUMENTS

| | | | |
|---|---|---|---|
| CN | 205681233 U | 11/2016 | |
| DE | 3812109 A1 | 10/1989 | |
| DE | 69402428 T2 | 10/1997 | |
| DE | 102005055013 B3 | 3/2007 | |
| EP | 0130374 A2 | 1/1985 | |
| EP | 0388269 B1 | 1/1994 | |
| EP | 1743100 B1 | 5/2008 | |
| GB | 2102504 A * | 2/1983 | .......... F04B 43/1246 |
| WO | WO-9114100 A1 | 9/1991 | |
| WO | WO-9403728 A1 | 2/1994 | |

OTHER PUBLICATIONS

International Search Report for Application No. PCT/EP2018/056705, dated Jun. 8, 2018.

* cited by examiner

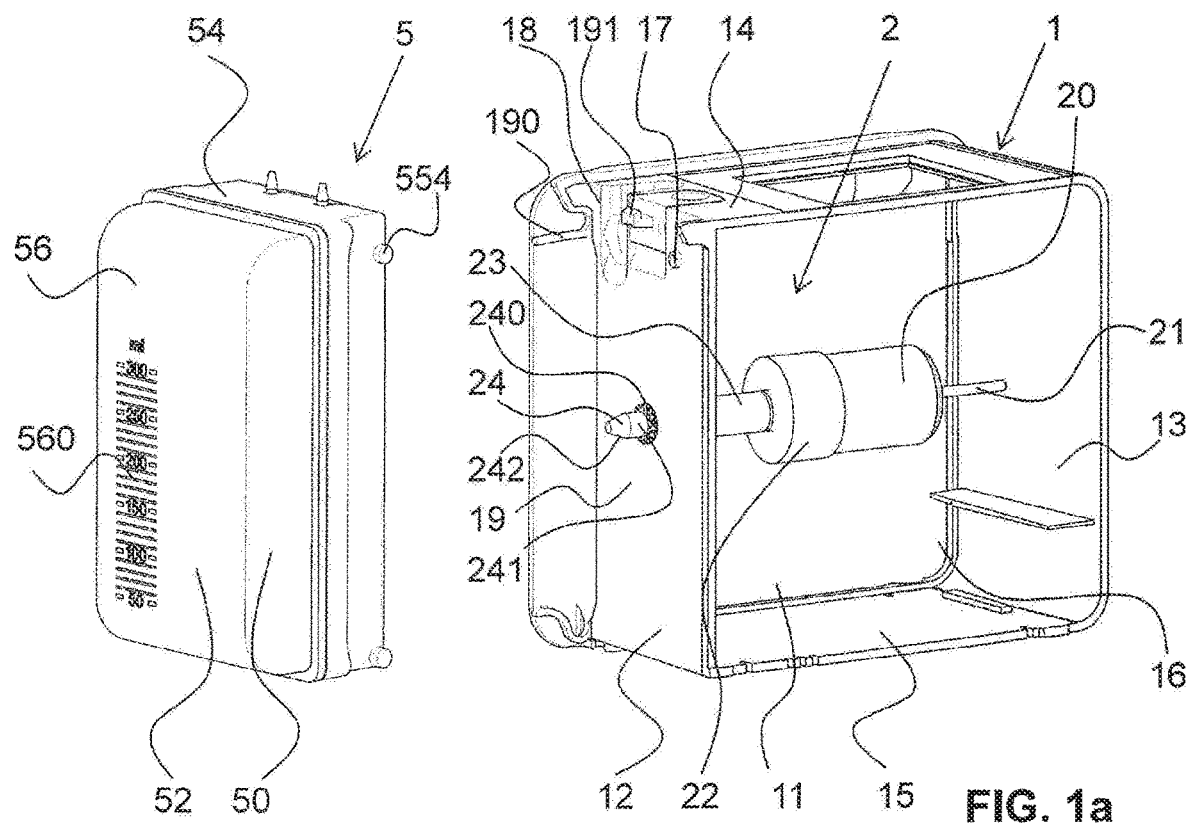
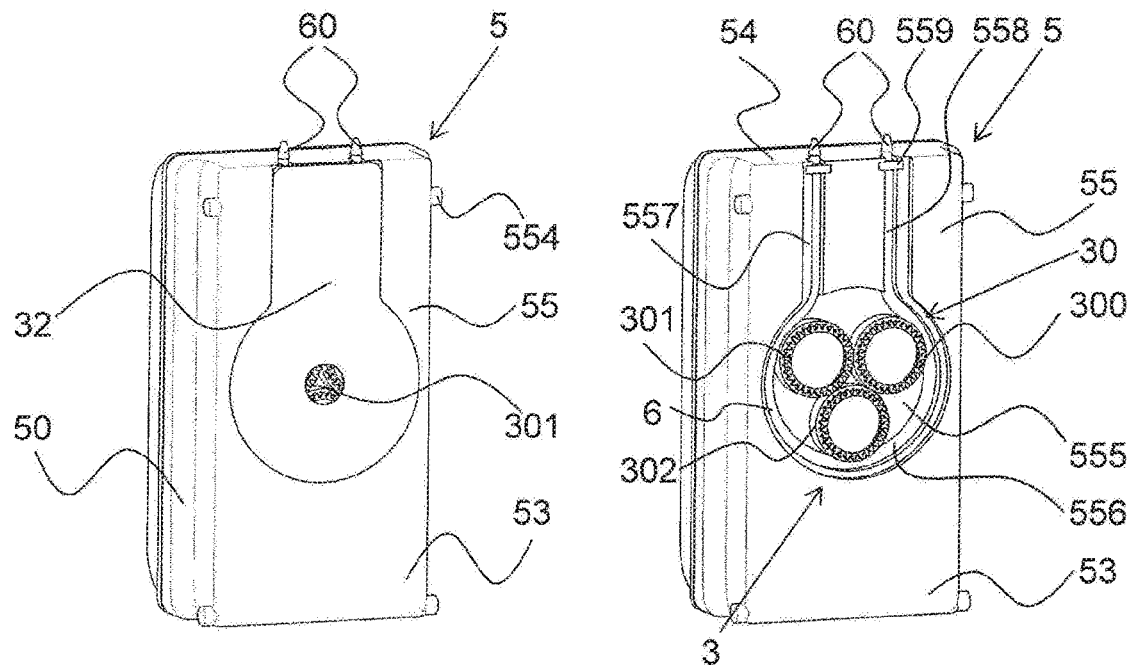
FIG. 1b
FIG. 1c

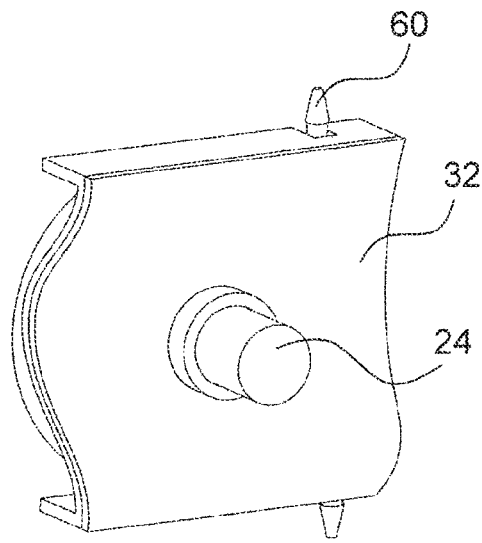
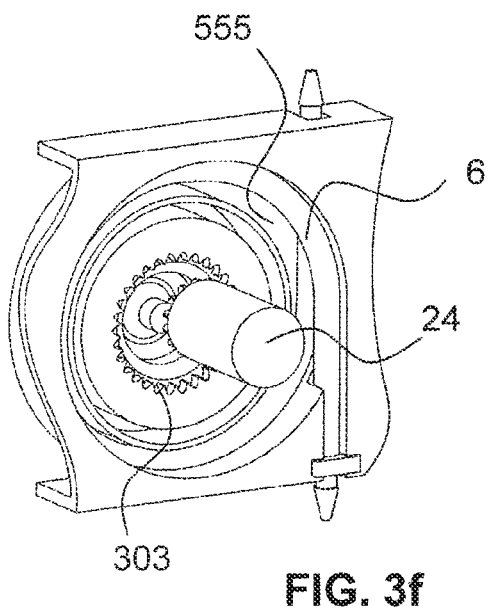
FIG. 3e  FIG. 3f
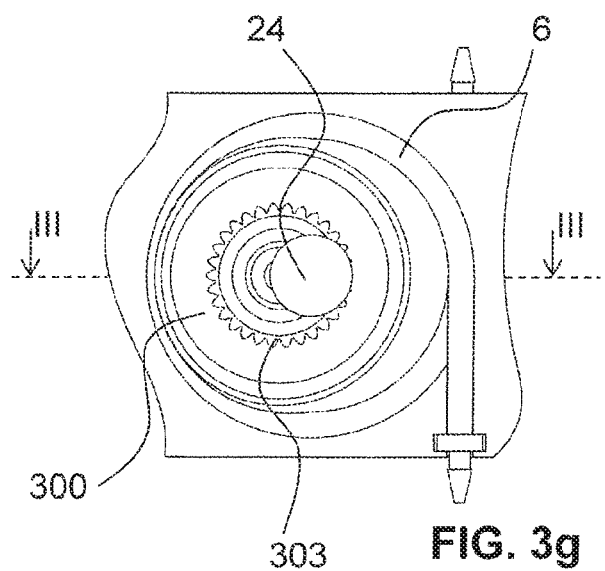
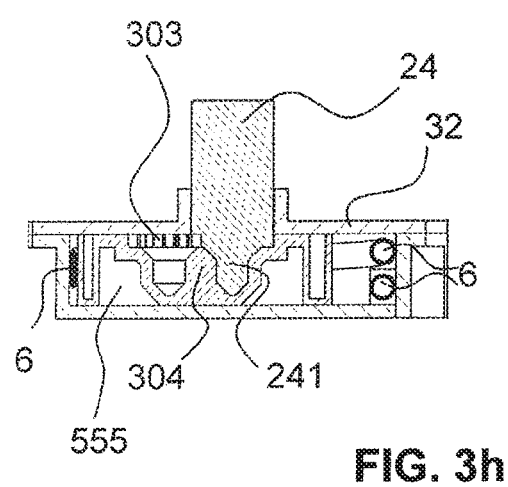
FIG. 3g  FIG. 3h

DEVICE WITH A PERISTALTIC PUMP UNIT WHICH CAN BE COUPLED

CROSS-REFERENCE TO RELATED APPLICATION

This present application is the US national phase of International Patent Application No. PCT/EP2018/056705, filed Mar. 16, 2018, which claims priority to European Application No. 17162577.5, filed Mar. 23, 2017. The priority application, EP 17162577.5, is hereby incorporated by reference in its entirety.

TECHNICAL FIELD

The present invention relates to a device for supplying and/or aspirating a fluid substance to or from a human or animal body and also relates to an attachment part of such a device. Devices of this kind are used in particular in the medical field, for example in negative-pressure wound therapy combined with instillation or irrigation, in ophthalmic surgery or in liposuction.

PRIOR ART

In the medical field, there are diverse applications where, on the one hand, bodily fluids or secretions are aspirated from body cavities or wounds by means of a pump and, on the other hand, a substance is supplied to the body. Possible areas of application relate, in particular, to negative-pressure wound therapy combined with instillation, to ophthalmic surgery and to liposuction (fat removal). Depending on the application, the aspiration and the supply are effected simultaneously, one after another and/or intermittently in an alternating manner. Of course, there are also many medical applications in which fluids are aspirated from the body only, without a substance being supplied. Equally, there are also applications in which a substance is supplied to the body only, without aspiration necessarily also having to take place.

If a fluid substance is aspirated, it can be in the form of secretions, for example, which are secreted from the body in a wound area, or in the form of instillation liquid or irrigation liquid or both.

The substance to be supplied can be, for example, a physiological or non-physiological saline solution, a medicament or a mixture thereof. The substance can serve, for example, for promoting wound healing, for preventing infections or for local anaesthesia. The substance can thus be delivered for irrigation or for therapeutic, diagnostic and/or preventive purposes.

For supplying the substance, in a manner similar to conventional infusion, a liquid pouch or a bottle filled with the substance to be supplied is often arranged at a height above the part of the body to be treated, such that the substance is supplied to the area to be treated through a supply line on account of hydrostatic pressure. Separately to this, bodily fluids are often aspirated by a vacuum pump via a corresponding line.

In order to better adjust and control the supply of the substance, and/or in order to be independent of the arrangement and in particular the height of the liquid container filled with the substance, systems are also well known in which the substance is supplied to the body by means of a pump, in particular a so-called peristaltic pump or hose pump. The aspiration of fluid substances from the body can also be effected by means of a peristaltic pump.

Peristaltic pumps or hose pumps of the type in question are disclosed, for example, in the documents EP 0 130 374 A2, DE 42 14 916 A1, DE 10 2005 055 013 B3, WO 94/03728, U.S. Pat. No. 4,181,476, WO 91/14100 and U.S. Pat. No. 5,927,956.

DE 38 12 109 A1 discloses a hose pump, but one which is designed to supply a cleaning agent in domestic appliances.

US 2014/0163487 discloses an appliance with two pumps, wherein the pump head of a peristaltic pump, which serves for supplying a substance to the body, is arranged on the outside surface of the pump assembly housing. A liquid container, which serves for receiving an instillation liquid, is attachable to the pump assembly housing. A hose guide is formed on the liquid container, on account of which the pump head, when the container is attached to the pump assembly housing, exerts a corresponding pumping action on the instillation hose running out of the container interior, in order thereby to pump the instillation liquid towards the body.

For cleaning purposes, and in particular to extend the useful life of the hose during storage and during transport, it may be desirable to reduce the strain placed on the hose when the hose pump is not in operation.

U.S. Pat. No. 4,218,197 and EP 0 388 269 B1 therefore each disclose a radially variable positioning of rollers on the pump head. Since the rollers are offset radially inwards, the pressure applied to the hose is reduced.

In the device disclosed in EP 1 743 100 B1, when the pump head is coupled to a drive unit, a spreader part of a coupling element is pushed between the roller elements arranged radially movably on the pump head. The roller elements are thus pressed outwards in the radial direction against the surrounding hose. The torque is transmitted from the coupling element to the pump head via driver pins which engage in recesses provided correspondingly on a holding plate that connects the roller elements. This solution has the disadvantage that, in the transmission of the torque from the coupling element to the pump, it is not possible to increase or reduce the rotational speed.

CN 205681233 U and CN 205117687 U disclose peristaltic pumps in which the pump head is formed by three roller elements that are interconnected by means of a connecting plate. The roller elements are movable to a certain extent in the radial direction and are driven by means of a shaft which is pushed between the roller elements and thus presses these in the radial direction against the hose. The torque is transmitted from the shaft to the pump head by frictional engagement. In order to achieve precisely defined pump properties, the roller elements have to be made from high-quality materials and with narrow production tolerances.

DE 694 02 428 T2 discloses a peristaltic pump cassette in which three rollers are arranged within a loop formed by a hose. In use of the peristaltic pump cassette, a drive axis is pushed forward centrally between the rollers, in order to push these radially outwardly against the hose. During operation, the power transmission from the drive axis to the rollers is effected by means of friction.

DISCLOSURE OF THE INVENTION

It is an object of the invention to make available a peristaltic pump unit which is simple to produce but which is nonetheless efficient.

In order to achieve this object, the present invention thus makes available a device for supplying and/or aspirating a fluid substance to or from a human or animal body, which device has a drive unit with a drive, in particular with a motor;

an attachment part which is attachable to the drive unit and which has a peristaltic pump unit with a pump head, a hose guide, and a hose placed in the hose guide, wherein the pump head has one or more roller elements which serve for rolling on the hose in order thereby to convey the fluid substance through the hose, in particular to convey it to the human or animal body or away from the human or animal body; and a coupling element which can be coupled to the pump head and which serves to transmit a movement from the drive to the pump head when the attachment part is attached as intended to the drive unit.

The pump head has a state in which it is decoupled from the coupling element, and in which the one or more roller elements apply no mechanical pressure or a comparatively low mechanical pressure to the hose, and in addition a state in which it is coupled to the coupling element, and in which the one or more roller elements are pressed by the coupling element against the hose with a comparatively high mechanical pressure.

The one or more roller elements, in the decoupled state, are movable freely and independently of each other within an area which is laterally delimited by the hose placed in the hose guide. The individual roller elements are not therefore connected to each other, but instead are arranged separately from each other in the area mentioned. The roller elements are therefore parts that are autonomous in terms of their freedom of movement. If several roller elements are present, they can generally touch each other in the decoupled state. The production costs are considerably reduced, and assembly made considerably easier, by the roller elements not being connected to each other.

The one or more roller elements are each preferably cylindrical.

The coupling element preferably has a first toothing area. In addition, the pump head preferably has a second toothing area which, in the coupled state, engages in the first toothing area of the coupling element in such a way that a movement of the coupling element is transmitted directly to the pump head. On account of the mutual engagement of the first toothing area and second toothing area, the transmission of the torque from the coupling element to the pump head during the operation of the peristaltic pump takes place in a particularly efficient manner and with an adjustable, clearly defined transmission or reduction ratio. The torque is transmitted in particular directly, that is to say not via an intermediate part, from the coupling element to the pump head and in particular to the one or more parts acting on the hose. If the pump head is formed by several roller elements, a mutual connection of the roller elements is not absolutely necessary for limiting their movement clearance or for ensuring a uniform movement profile. Even if the individual roller elements touch each other during operation, the frictional force generated between the roller elements has no influence on their movement, since the force flow from the coupling element to the individual roller elements is considerably more efficient. Even with very high pump output rates, and with a correspondingly high pressure in the hose, the transmission or reduction ratio between coupling element and pump head is clearly defined.

In an alternative embodiment, the transmission of the movement from the coupling element to the pump head, and in particular to the one or more roller elements, can also be effected by means of a purely frictional force. The corresponding surfaces of the coupling element and of the one or more roller wheels, which can then be of a cylindrical configuration for example, are then advantageously configured in such a way that they have a high coefficient of friction.

In the coupled state, the coupling element thus presses the pump head or parts of the pump head, in particular one or more roller elements, outwards in the radial direction against the hose. In the case of several roller elements, the coupling element can also be designated as a spreader element. In the decoupled state, by comparison with the coupled state, the pump head or parts thereof are pushed radially inwards on account of the pressure of the hose. The material of the hose is therefore subjected to barely any load, as a result of which the hose has a greater useful life in terms of transport and storage and/or can be configured with a smaller wall thickness. With a smaller wall thickness of the hose which usually is made from silicon, the work to be effected by the drive during operation is additionally reduced.

The one or more roller elements can each have a certain lateral play in the decoupled state.

In the coupled state, the pump head and in particular the roller elements thereof are preferably each pressed against the hose by the coupling element in such a way that, by comparison with the decoupled state, they deform in a way that is clearly visible to the human eye, in particular elastically. A certain spring action is thus obtained, as a result of which a clearly defined pressing force on the hose is achieved even in cases of relatively large manufacturing tolerances.

When attaching the attachment part to the drive unit, in order to couple the coupling element to the pump head and continuously increase the pressing force on the hose, the coupling element advantageously has a conically shaped portion, in particular end portion.

Advantageously, the coupling element moreover has a cylindrical portion which, in the coupled state, serves to press the one or more roller elements against the hose. Advantageously, the pressing does not then take place via toothing areas that may possibly be present.

The coupling element can be a part of the drive unit. However, it can also be a part of the attachment part.

The attachment part can in particular be a fluid container for collecting or making available a fluid. It can be a disposable part that is discarded after just one use.

The one or more roller elements are each preferably formed by a hollow wheel. A hollow wheel is a substantially circular object with a radially outwardly directed outer face and a radially inwardly directed inner face. A toothed ring is usually formed on the outer and/or inner face.

The second toothing area can thus be formed in each case by an outer toothed ring provided on the one or more hollow wheels.

However, the second toothing area can also be an inner toothed ring provided on the hollow wheel. In such an embodiment, the hollow wheel preferably has a centrally arranged circulating element which, in the coupled state, bears on the coupling element.

The pump head is preferably produced entirely from a plastic in an injection moulding method, in particular from polypropylene (PP). However, it can also be produced from other materials, in particular organic materials.

The present invention moreover relates to an attachment part of a device for supplying and/or aspirating a fluid substance to or from a human or animal body, in particular to an attachment part of a device according to the above explanations. The attachment part has a peristaltic pump unit with a pump head, a hose guide, and a hose placed in the hose guide, wherein the pump head has one or more roller elements which serve for rolling on the hose in order thereby to convey the fluid substance through the hose, in particular to convey it to the human or animal body or away from the human or animal body. The pump head can be coupled to a coupling element which serves to transmit a movement from a drive to the pump head. In a state decoupled from the coupling element, the one or more roller elements apply no mechanical pressure or a comparatively low mechanical pressure to the hose, but can be coupled to the coupling element in such a way that, in a coupled state, the one or more roller elements are pressed by the coupling element against the hose with a comparatively high mechanical pressure. The one or more roller elements, in the decoupled state, are movable freely and independently of each other within an area which is laterally delimited by the hose placed in the hose guide.

BRIEF DESCRIPTION OF THE DRAWINGS

Preferred embodiments of the invention are described below with reference to the drawings which serve simply for explanatory purposes and are not to be interpreted as limiting the invention. In the drawing:

FIG. 1a shows a perspective view of a schematically depicted device in a first embodiment according to the invention, with an attachment part in the form of a fluid-collecting container and with a pump assembly housing, the front wall of the pump assembly housing being omitted;

FIG. 1b shows a second perspective view of the fluid-collecting container of the device shown in FIG. 1a, from another angle;

FIG. 1c shows the same view of the fluid-collecting container shown in FIG. 1b, but with the cover removed;

FIG. 3b in the decoupled state and with the cover removed;

FIG. 3e shows a perspective view of the attachment part from FIG. 3a and of the coupling element from FIG. 3a, in the coupled state;

FIG. 3f shows the attachment part from FIG. 3e with coupling element in the coupled state and with the cover removed;

FIG. 3g shows a plan view of the peristaltic pump unit of the attachment part from FIG. 3f with coupling element in the coupled state and with the cover removed; and FIG. 3h shows a central cross-sectional view along the line III-III through the attachment part from FIG. 3g with coupling element in the coupled state and with the cover removed.

DESCRIPTION OF PREFERRED EMBODIMENTS

Figure 1D:
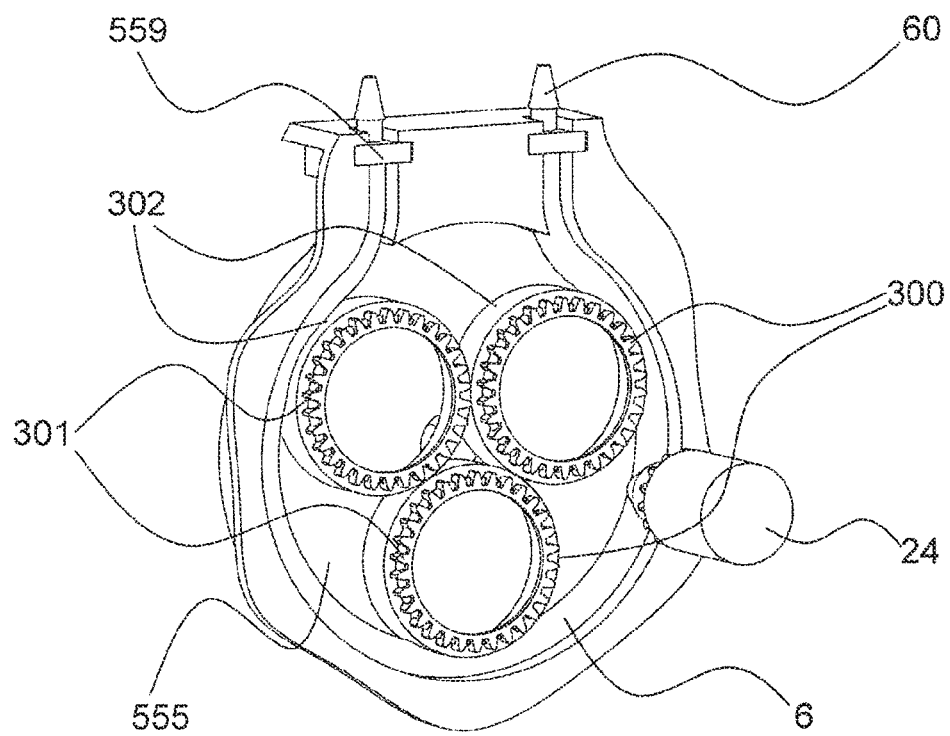
FIG. 1d shows a first perspective detail view of the peristaltic pump unit of the fluid-collecting container shown in FIG. 1c, including the coupling element of the pump assembly housing shown in FIG. 1a, in the decoupled state.
Figure 1E:
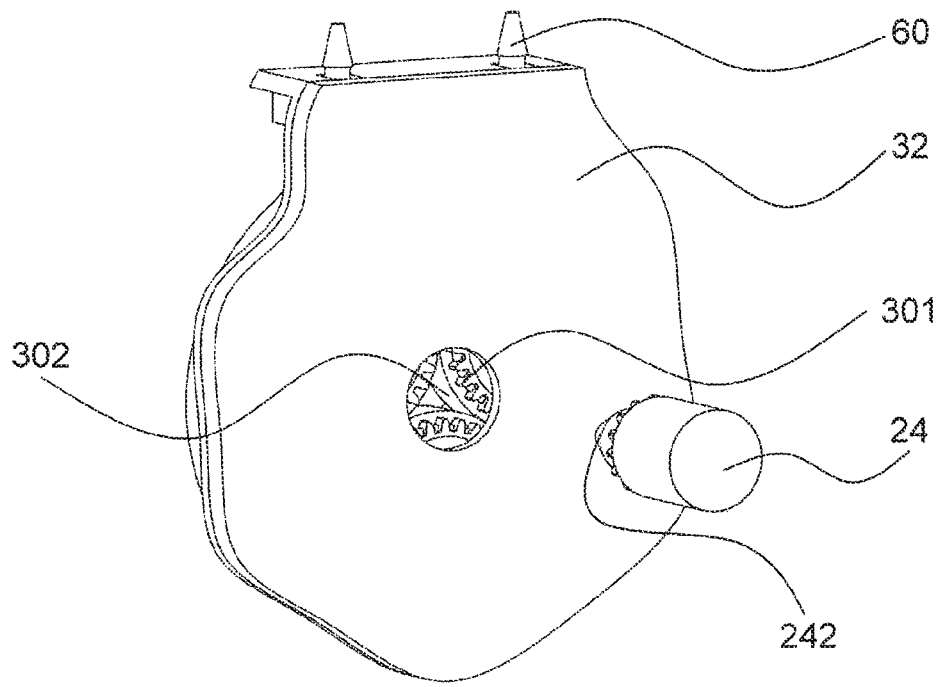
FIG. 1e shows a perspective detail view of the peristaltic pump unit of the fluid-collecting container shown in FIG. 1b, including the coupling element of the pump assembly housing shown in FIG. 1a, in the decoupled state.

FIGS. 1a to 3h show different embodiments of devices according to the invention and of attachment parts according to the invention. The devices shown in FIGS. 1a to 3h are suitable for instillation/irrigation treatment of wounds on the human or animal body, particularly in combination with negative-pressure treatment. Accordingly, the following explanations refer in each case to the use of the devices in instillation/irrigation treatment, if appropriate in combination with negative-pressure treatment. However, it would also be possible in principle to use these devices, with a correspondingly adapted design, for example for catheter flushing, ophthalmic surgery, liposuction or another medical application.

Elements having an identical or similar technical function and action are provided in each case in the different embodiments in FIGS. 1a to 3h with the same reference signs.

The device in the first embodiment according to the invention, which is shown in FIGS. 1a to 1h, has a pump assembly housing 1 with an attachment part, attachable thereto, in the form of a fluid-collecting container 5 (FIG. 1).

Whereas the pump assembly housing 1, including its interior, is usually designed for multiple uses and therefore for the longest possible useful life, the fluid-collecting container in many applications is, in particular for hygiene reasons, a disposable article that is discarded after a single use, which often lasts only a few days or hours.

The pump assembly housing 1 has an overall substantially cuboid shape with a front wall (not shown in FIG. 1a), a rear wall 11, a first side wall 12 and a second side wall 13, and also a top wall 14 and a bottom wall 15. The front wall and the rear wall 11 have one wall edge each, which wall edges protrude from the first side wall 12 that is arranged between them. The fluid-collecting container 5 is held between these wall edges and, as a result, can be secured easily, but nevertheless securely and in a protected manner, on the pump assembly housing 1.

For suspending and holding the fluid-collecting container 5 on the pump assembly housing 1, receiving hooks 190, in which correspondingly configured and arranged pins 554 of the fluid-collecting container 5 are able to engage, are provided on the pump assembly housing 1. The pump assembly housing 1 can have a retaining lug 191 which is mounted on a spring-loaded element and which is designed to engage with a snap fit into a latching notch formed on the fluid-collecting container 5 (but not shown in the figures) in order to secure the fluid-collecting container 5 on the pump assembly housing. In order to release the latching connection between the retaining lug 191 and the latching notch, the spring-loaded element, on which the retaining lug 191 is mounted, can be pressed downward counter to the spring force.

The protruding wall edges of the front wall and of the rear wall 11 and also the receiving hooks 190 and the retaining lug 191 together form a container holder 19 of the fluid-collecting container 5.

The pump assembly housing 1 has a housing-side vacuum port 17 which, when the fluid-collecting container 5 is mounted on the pump assembly housing 1, is coupled to a container-side vacuum port which is correspondingly provided on the fluid-collecting container 5 but which is not shown in the figures, such that a vacuum can be generated in the interior of the fluid-collecting container 5 via the housing-side and the container-side vacuum port in order to aspirate bodily fluids via a secretion line (not shown in the figures) and collect them in the fluid-collecting container 5. The secretion line connects the fluid-collecting container 5 to a cavity or wound of a patient, from which bodily fluids are to be aspirated.

In addition, an adapter receiver 18, which serves to receive a hose adapter (not shown in the figures), is provided inside the first side wall 12. The hose adapter connects the secretion line to the interior of the fluid-collecting container 5 via a container-side secretion port which is provided on the fluid-collecting container 5, but which is likewise not shown in the figures.

A drivetrain 2 with a motor 20 and a motor shaft 21 connected to the motor 20 is accommodated in an interior 16 of the pump assembly housing 1. The pump assembly housing 1 forms a drive unit together with the drivetrain 2 and with further elements arranged, if need be, in the interior 16.

By way of a first end region, the motor shaft 21 directly drives a diaphragm pump, which is not shown in FIG. 1a for reasons of representation. By means of the diaphragm pump, which is arranged in the interior 16 of the pump assembly housing 1, a vacuum can be generated in order to aspirate bodily fluids through the secretion line on the housing-side vacuum port 17. By way of a second end region, which is not visible in FIG. 1, the motor shaft 21 is connected to a freewheel and/or gearing unit 22 which connects the motor shaft 21 to a drive shaft 23. The drive shaft 23, which extends along the rotation axis of the motor shaft 21, projects through the first side wall 12.

On the outside of the pump assembly housing 1, a coupling element 24 is mounted in a rotationally fixed manner on the end of the drive shaft 23. The coupling element 24 has a peripheral toothed ring 240 with teeth which are arranged at regular intervals and which extend radially outwards. The toothed ring 240 is arranged directly on the outside of the first side wall 12 and can even bear on the latter. Directly adjacent to the toothed ring 240, the coupling element 24 has a cylindrical portion 241 which, at its outer end, merges into a conical portion 242. The conical portion 242, which forms the outer end of the coupling element 24, tapers conically outwards and thus towards the fluid-collecting container 5.

A pump head 30 of a peristaltic pump unit 3 (FIG. 1c) integrated in the fluid-collecting container 5 can be driven via the coupling element 24 when the fluid-collecting container 5 is mounted as intended on the pump assembly housing 1. The coupling element 24 therefore serves to transmit the movement of the drive shaft 23, generated by motor 20, to the pump head 30 of the peristaltic pump unit 3.

The motor 20 therefore serves both for driving the diaphragm pump and for driving the peristaltic pump unit 3. In an alternative embodiment, two separate motors can of course also be provided in the interior 16 of the pump assembly housing, one serving to drive the diaphragm pump and the other serving to drive the peristaltic pump unit 3.

As can be seen particularly clearly in FIGS. 1a and 1b, the fluid-collecting container 5 has a front wall 50, a rear wall (not visible in the figures), two side walls 52 and 53, and also a top wall 54 and a bottom wall, which is likewise not visible in the figures. These walls are formed by a base part 55, which is produced from an opaque material, and a translucent part 56. A fill level graduation 560 is provided on the side wall 52 which is formed exclusively by the translucent part 56.

The side wall 53, which is formed exclusively by the base part 55, has a centrally arranged, ring-shaped depression 555 on its outer face. In the radial direction, the depression 555 is delimited substantially about the circumference by a boundary wall 556. In the base part 55, an inlet channel 557 and an outlet channel 558 are additionally formed, which each extend rectilinearly and parallel to each other from the upper wall 54 into the depression 555.

The inlet channel 557, the outlet channel 558 and the boundary wall 556 together form a hose guide for an instillation hose 6. The latter is placed in the hose guide in such a way that it extends through the inlet channel 557 into the recess 555 and there extends along the boundary wall 556 and substantially around the pump head 30. By way of the outlet channel 558, the instillation hose 6 leads back out of the fluid-collecting container 5. In order to prevent slipping of the instillation hose 6, particularly along its longitudinal direction, a holding element 559 is fixed thereon in the areas where the inlet channel 557 and the outlet channel 558 open outwards in the upper wall 54. The holding elements 559 are placed in recesses provided for them in the inlet channel 557 and in the outlet channel 558, such that longitudinal displacement and rotation of the instillation hose 6 are rendered impossible.

Attachment elements 60 which serve for the attachment of further hoses are provided at each of the ends of the instillation hose 6. For example, one of the attachment elements 60 can be connected via a first further hose to a container in which the substance to be supplied to a patient is stored. The other attachment element 60 can then be connected, for example, via a second further hose to a wound area, such that the substance is conveyed by means of the peristaltic pump 3 out of the container and through the instillation hose 6 to the wound.

The pump head 30 of a peristaltic pump unit 3 is arranged inside the depression 555. In the present illustrative embodiment, the pump head 30 is formed by three identically configured roller elements 300. The roller elements 300 are each formed by hollow wheels, which lie flat in the depression 555 and are freely movable there.

As can be seen particularly clearly from FIG. 1d, the roller elements 300 each have an outer toothed ring 301 and a radially outwardly directed surface 302. The roller elements 300, which are each preferably produced in one piece from a plastic, form the satellite wheels of the peristaltic pump 3.

In the situation shown in FIG. 1d, the pump head 30 formed by the roller elements 300 is located in a decoupled state, in which the coupling element 24 is arranged at a distance from the pump head 30. In other words, the fluid-collecting container 5 is not attached to the pump assembly housing 1. In this decoupled state, the roller elements 300 are freely movable within the space of the depression 555 laterally delimited by the instillation hose 6. In particular, there is no connection present between the individual roller wheels 300, that is to say they can be rotated and moved in any desired way and independently of each other.

The roller wheels 300 are arranged in a triangle and lie with their cylindrical surfaces 302 on one another and also on the instillation hose 6. In the decoupled state shown in FIG. 1d, the roller wheels 300 apply only a slight pressure to the instillation hose 6. It would also be conceivable that they apply no pressure at all to the instillation hose 6 and do not even touch the latter in the decoupled state. However, the fact that the roller wheels 300 bear on each other and on the instillation hose 6 as per FIG. 1d has the advantage of preventing the roller wheels 300 from rattling or from hitting against each other, e.g. during transport of the fluid-collecting container. As an alternative or in addition, positioning elements 57 can also be provided inside the depression 555 in order to define the position of the rollers during storage (see FIG. 2c).

Since the roller wheels in the decoupled state apply no pressure or only slight pressure to the instillation hose 6, damage to the instillation hose 6 during transport or storage is avoided. Moreover, the instillation hose 6 can be completely sterilized in its interior. The material of the instillation hose 6 is unloaded and thus has a greater useful life. The demands placed on the instillation hose 6 are thus reduced, and it can in particular be produced with a thinner wall, as a result of which the production costs are also reduced. The same applies to the roller wheels 300, on which less demand is likewise placed on account of the unloaded state, and which can therefore be produced with a thinner wall and from a comparatively favourable material suitable for injection moulding, for example polypropylene (PP). A thinner wall of the instillation hose 6 additionally has the effect that the deformability to be provided from the motor 20 via the drivetrain is reduced. The motor 20 can thus be operated with a lower motor power, or a motor 20 can be used that is of smaller dimensions.

Figure 1F:
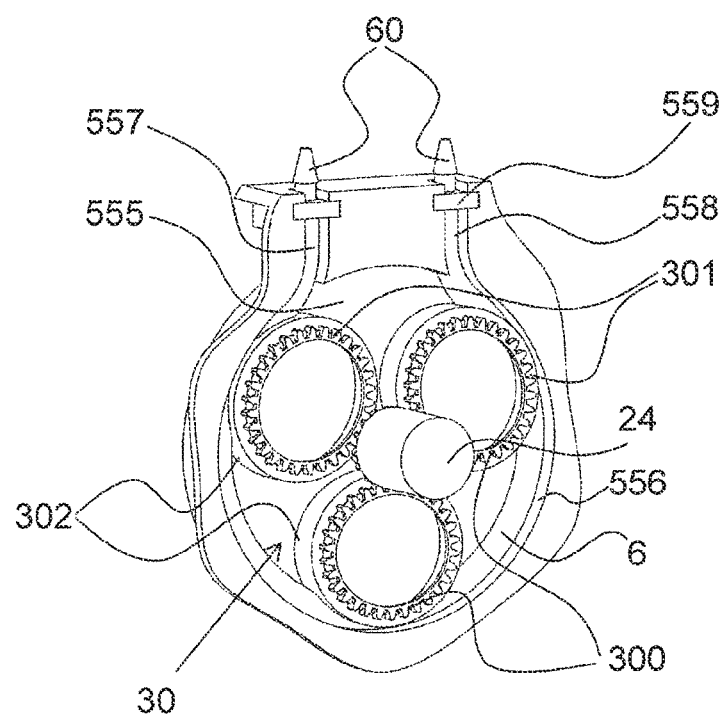
FIG. 1f shows a perspective detail view of the peristaltic pump unit of the fluid-collecting container shown in FIG. 1c, including the coupling element of the pump assembly housing shown in FIG. 1a, in the coupled state.

When attaching the fluid-collecting container 5 to the pump assembly housing 1, the coupling element 24, as shown in FIG. 1f, is pushed between the roller wheels 300. The conical portion 242 then presses the roller wheels 300 outwards in the radial direction and against the instillation hose 6. The instillation hose 6 is pressed by the roller wheels 300 against the boundary wall 556 and thereby deforms. When the coupling element 24 is advanced fully between the roller wheels 300, the conical portion 242 of the coupling element 24 bears on the cylindrical surfaces 302 of the roller wheels 300 and thus holds the roller wheels 300 in their position pressed against the instillation hose 6. The toothed ring 240 of the coupling element 24 is then in meshing engagement with the outer toothed rings 301 of the roller wheels 300. This state of the pump head 30, when the coupling element 24 is advanced fully between the roller wheels 300, is designated as the coupled state.

On account of the toothed ring 240 engaging with the outer toothed rings 301, a rotation movement of the coupling element 24, caused by the motor 20, is transmitted directly to the roller wheels 300, which thus roll with their cylindrical surfaces 302 on the instillation hose 6 and thus bring about the desired pump action of the peristaltic pump 3. On account of the mutual toothing, a clearly defined reduction of the rotation movement of the coupling element 24 to that of the pump head 30 or the roller wheels 300 is achieved.

Figure 1G:
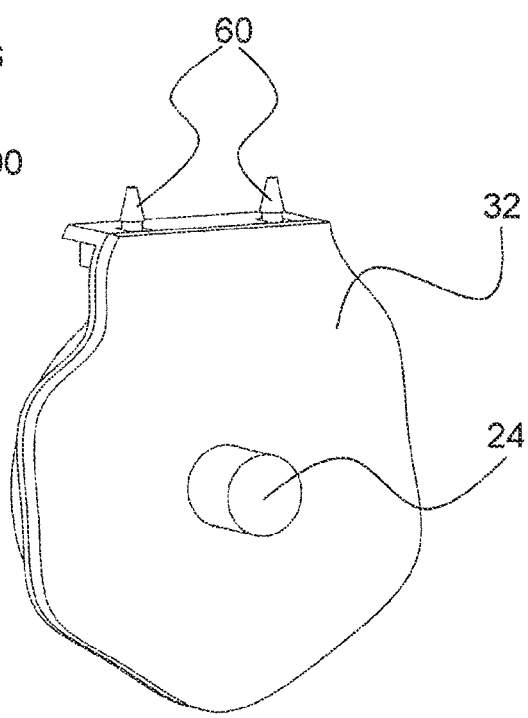
FIG. 1g shows a perspective detail view of the peristaltic pump unit of the fluid-collecting container shown in FIG. 1b, including the coupling element of the pump assembly housing shown in FIG. 1a, in the coupled state.
Figure 1H:
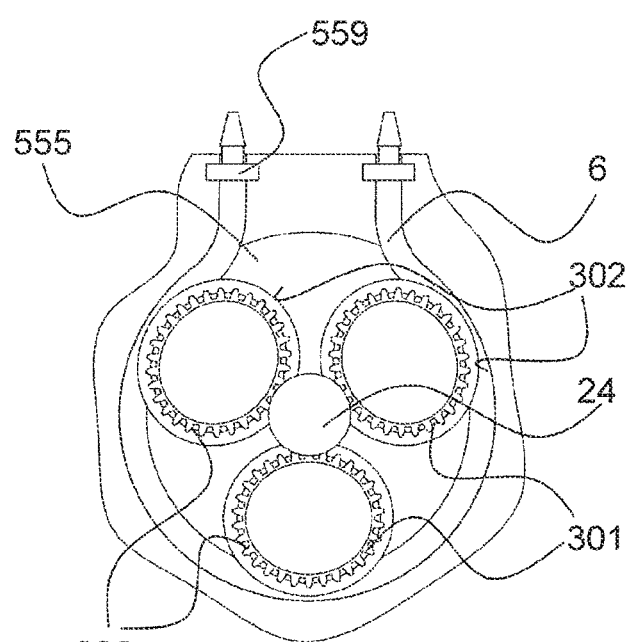
FIG. 1h shows a plan view of the peristaltic pump unit of the fluid-collecting container shown in FIG. 1c, including the coupling element of the pump assembly housing shown in FIG. 1a, in the coupled state.

In the coupled state, as shown in particular in FIG. 1h, the roller wheels 300 can be elastically deformed in relation to the decoupled state, on account of the pressure between the coupling element 24 and the instillation hose 6. This is not a disadvantage, and indeed it may even be desirable. The easy deformation of the roller wheels 300, in the present case from a circular shape to a slightly oval shape, results in a spring action. It is thus possible to achieve a uniform pressing force on the instillation hose 6 by the various roller wheels 300, even in cases of relatively large manufacturing tolerances.

As can be seen in FIGS. 1b, 1c and 1g, the fluid-collecting container 5 has a cover 32, which covers the depression 555 and also the inlet channel 557 and the outlet channel 558. In a central area of the depression 555, the cover 32 has a circular cutout through which the coupling element 24 protrudes when the fluid-collecting container 5 is attached to the pump assembly housing 1.

FIGS. 2a to 2f show a further embodiment of an attachment part for a device according to the invention. Here, the attachment part is a peristaltic cassette 5' which, for example, can be arranged as intermediate part between a fluid-collecting container and the pump assembly housing 1. The peristaltic cassette 5' has a housing with a hose guide for the instillation hose 6, which is guided through the housing. Advantageously, basically all the parts of the peristaltic cassette 5' are produced from a plastic in an injection moulding method.

Figure 2A:
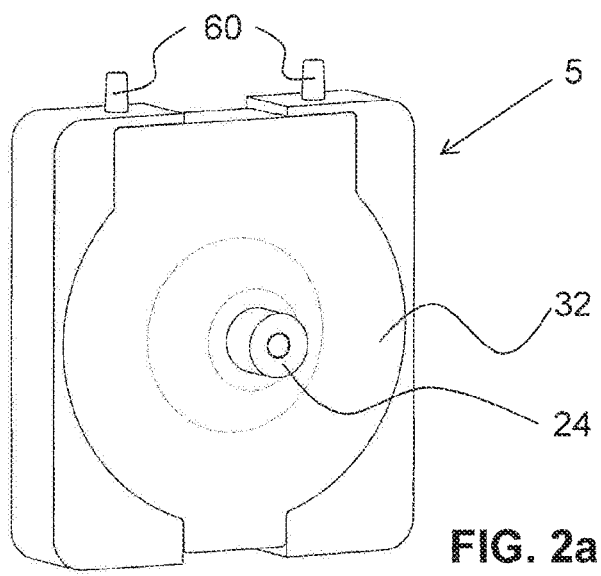
FIG. 2a shows a perspective view of an attachment part in the form of a peristaltic cassette of a device in a second embodiment according to the invention, in the decoupled state.
Figure 2B:
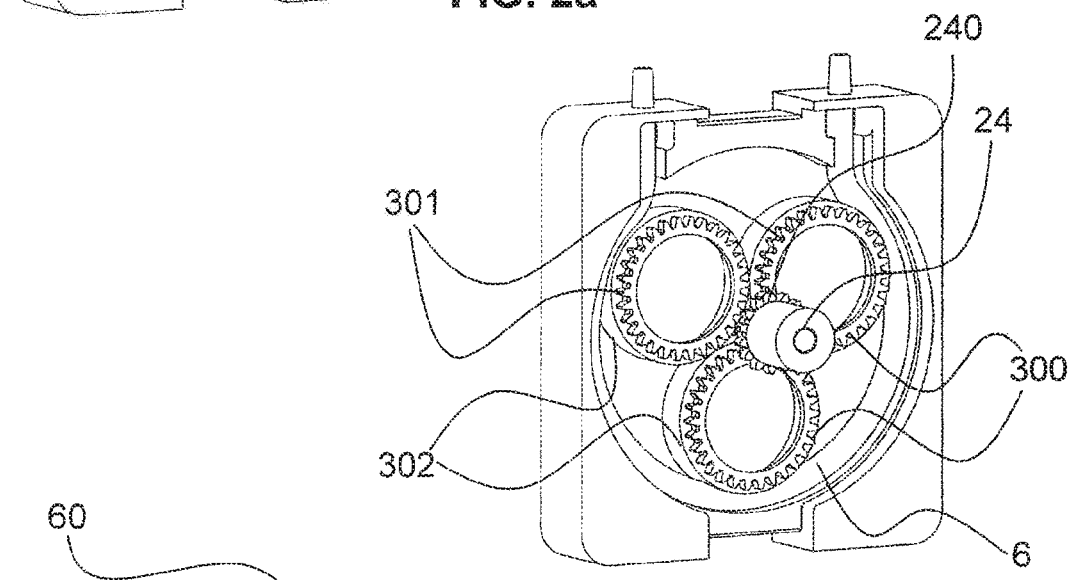
FIG. 2b shows the peristaltic cassette shown in FIG. 2a with the pump head in the decoupled state and with the cover removed.
Figure 2C:
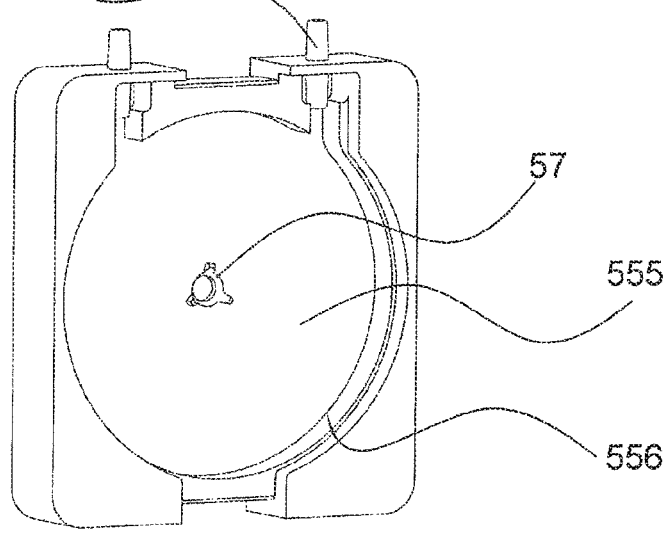
FIG. 2c shows the peristaltic cassette shown in FIG. 2a with the cover removed and without pump head, instillation hose and coupling element.
Figure 2D:
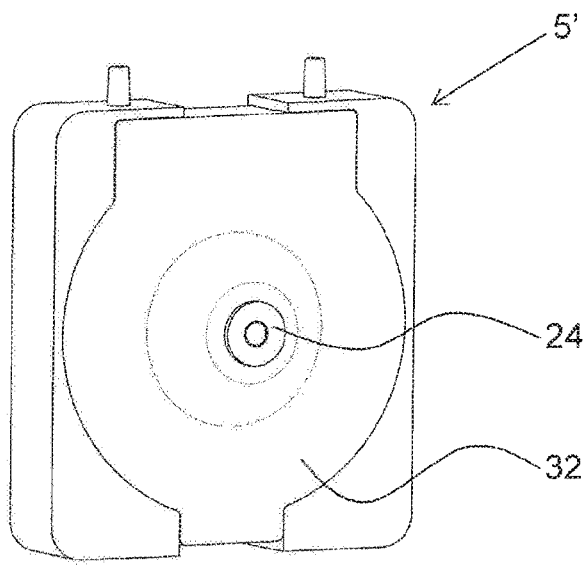
FIG. 2d shows the peristaltic cassette shown in FIG. 2a in the coupled state.
Figure 2E:
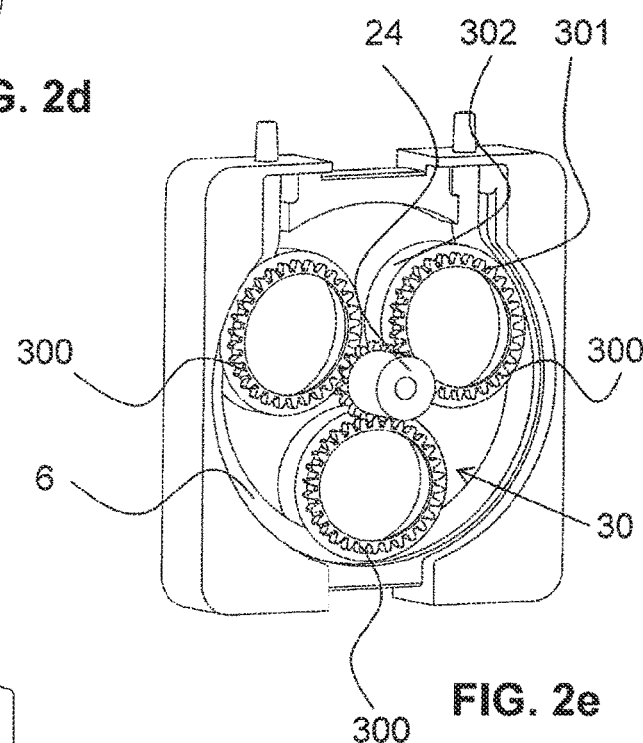
FIG. 2e shows the peristaltic cassette shown in FIG. 2a with the pump head in the coupled state and with the cover removed.
Figure 2F:
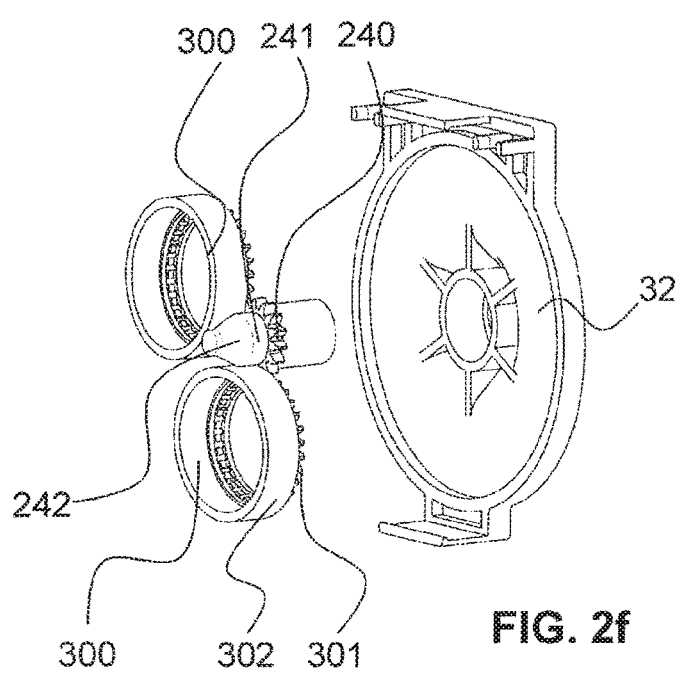
FIG. 2f shows a perspective view of the cover, the coupling element and of part of the pump head of the peristaltic cassette shown in FIG. 2a in the coupled state.

The peristaltic cassette 5' has overall a substantially cuboid, thin external form. As can be seen in particular in FIG. 2c, the housing of the peristaltic cassette 5' has a substantially circular depression 555 inside which a pump head 30 of a peristaltic pump 3 is arranged in a freely rotatable manner (FIG. 2b). The pump head 30 is designed identically to that in the embodiment shown in FIGS. 1a to 1h. It likewise has several roller elements 300 which serve to roll on the instillation hose 6 placed in the depression 555 around the pump head 30 and, by means of mechanical deformation of the hose, to convey a substance through the instillation hose 6 to the wound area.

In contrast to the embodiment shown in FIGS. 1a to 1h, the coupling element 24 in the embodiment in FIGS. 2a to 2f forms a part of the attachment part, in this case of the peristaltic cassette 5'. In the area around the central cutout, the cover 32 has a conical bulge which, on the side facing towards the depression 555, is strengthened by means of ribs (see FIG. 2f). As a result of the toothed ring 240 abutting against these ribs, it is impossible for the coupling element 24 to fall out of the peristaltic cassette 5'. In order to bring the coupling element 24 to the state in which it is coupled to the pump head 30, it can simply be pressed from the outside through the cutout provided in the cover 32 and into the peristaltic cassette 5'. On its outwardly facing side, the coupling element has an engagement structure, such that the pump head 30 can be set in a rotation movement by the drive unit via the coupling element 24.

The embodiments shown in FIGS. 1a to 2f can in principle have any desired number of roller wheels 300, i.e. in particular also just one roller wheel, two, or more than three. The cylindrical portion 241 of the coupling element 24 and the cylindrical surface 302 of the roller elements 300 afford the advantage that the pressing force of the roller elements 300 on the instillation hose 6 does not have to be transmitted via the toothed rings 240 and 301. In principle, however, the cylindrical portion and the cylindrical surface 302 can also be omitted. In alternative embodiments, the peristaltic pumps 3 shown in the embodiments in FIGS. 1a to 2f can also serve for aspirating fluids from the human or animal body. In the case of torque being transmitted purely by frictional engagement, the toothed rings 240 and 301 can be omitted.

An attachment part in a further embodiment according to the invention is shown in FIGS. 3a to 3h. The attachment part can be, for example, a fluid container or a peristaltic cassette. If it is a fluid container, the latter can serve for collecting aspirated fluids or for making available a substance that is to be supplied. In the same way as in the embodiments shown in FIGS. 1a to 2f, the pump head 30 here is also arranged inside the circular depression 555 of a housing. Here, an instillation hose 6 is also placed in the depression 555, which instillation hose 6 extends along the boundary wall 556 around the pump head 30. However, in contrast to the embodiments shown in FIGS. 1a to 3h, the instillation hose 6 here does not cross over itself in the interior of the attachment part and is guided out of the latter on opposite sides.

The direction of flow of the fluid through the inlet channel 557 and through the outlet channel (not visible in FIGS. 3a-3h) is from the top downwards along the force of gravity. A return flow of the fluid is thereby prevented. By virtue of the inlet channel 557 and the outlet channel opening out on opposite sides of the housing, and on account of the arrangement of the attachment elements 60 on opposite sides of the housing, it is possible to avoid kinking of the hose as it is put in place by the specialist medical personnel.

The pump head 30 of the embodiment in FIGS. 3a to 3h has only a single roller element 300. As can be seen from FIG. 3c, in the decoupled state, this roller element 300 substantially completely fills the space delimited laterally by the instillation hose 6, without thereby applying a substantial pressure to the instillation hose 6. The roller element 300 has a pot-like shape with a centrally arranged circular depression. In its opening area, the depression is bounded by an inner toothed ring 303, which has a large number of radially inwardly extending teeth arranged at regular intervals. The roller wheel 300 can thus also be designated here as a hollow wheel.

Centrally inside the depression bounded by the inner toothed ring 303, the roller wheel 300 has a revolving cam 304. The revolving cam 304 has a cylindrical outer surface, which is adjoined by a conically tapering end portion.

Figure 3A:
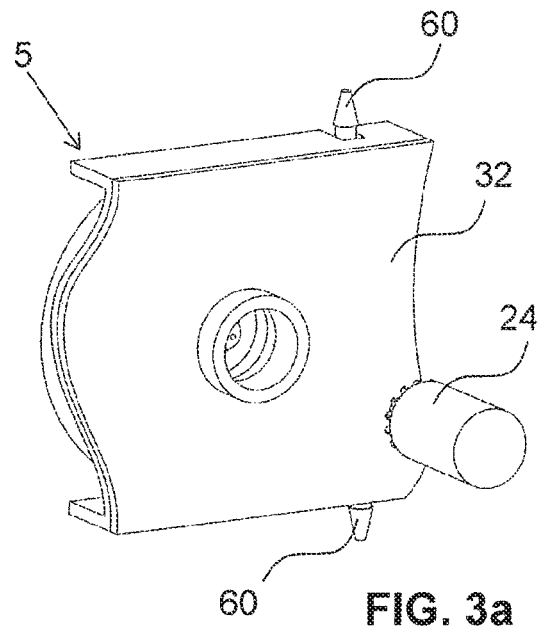
FIG. 3a shows a perspective view of an attachment part and of a coupling element of a device in a third embodiment according to the invention, in the decoupled state.
Figure 3B:
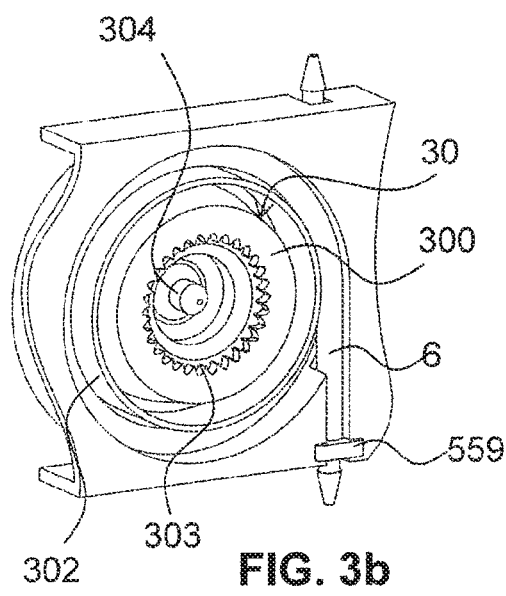
FIG. 3b shows the attachment part from FIG. 3a in the decoupled state and with the cover removed.
Figure 3C:
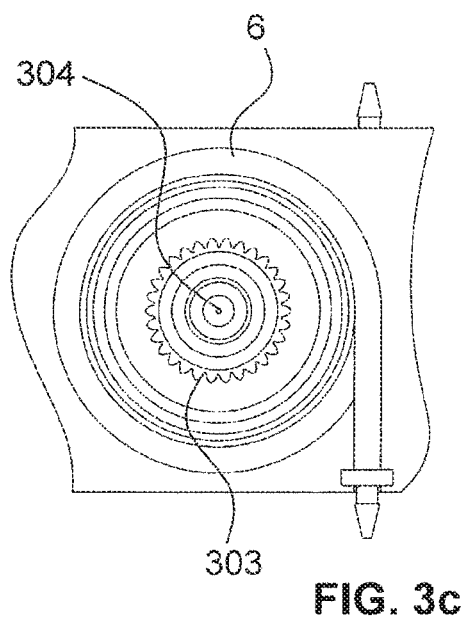
FIG. 3c shows a plan view of the peristaltic pump unit of there attachment part from FIG.
Figure 3D:
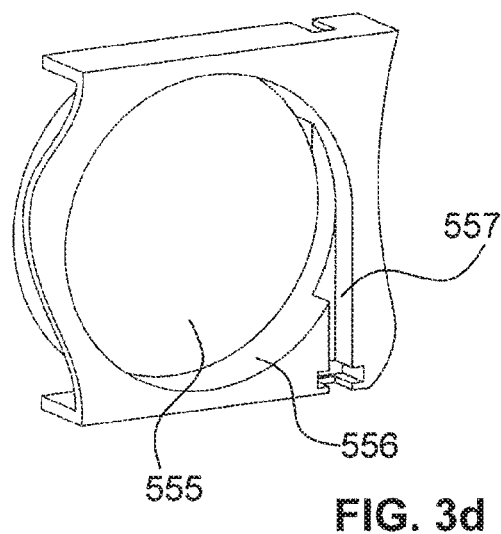
FIG. 3d shows a perspective view of the attachment part from FIG. 3a without cover, pump head and instillation hose.

The roller wheel 300 has a cylindrical outer surface 302, which is formed by a peripheral edge area of the pump head 30 (see FIG. 3b). Between the edge area and an inner area, on the inner face of which the inner toothed ring 303 is formed, the roller wheel 300 has a peripheral depression. By virtue of this peripheral depression, the cylindrical outer surface 302 is elastically deformable to a certain extent.

When coupling the coupling element 24, which can be but does not have to be part of the attachment part, it is pushed through a cutout provided in the cover 32 and into the central circular depression of the roller element 300. The coupling element 24 slides with its conical portion 242 along the conical end portion of the revolving cam 304 and thus presses the roller element 300 radially towards the instillation hose 6. In the fully coupled state, the coupling element 24, as can be seen in FIG. 3h, bears with its cylindrical portion 241 laterally on the cylindrical outer surface of the revolving cam 304, as a result of which the roller wheel 300 is held in its position and the instillation hose 6 is squeezed together. On account of the circular depression, the roller wheel 300 is able to easily deform in the area of its cylindrical outer surface 302, as can be seen in FIG. 3g and in particular in FIG. 3h.

In the coupled state, the outer toothed ring 240 of the coupling element 24 is additionally in meshing engagement with the inner toothed ring 303 of the roller element 300. In this way, a rotation movement of the coupling element 24 is transmitted directly to the roller element 300, such that, in the coupled state, the pump head 30 can be set in a rotation movement via the coupling element 24 by means of an external drive. The pump head 30 formed by the roller element 300 thus rolls on the instillation hose 6 and thereby generates the desired pump action.

The embodiment shown in FIGS. 3a to 3h has the particular advantage that the pressing force is transmitted from the coupling element 24 to the pump head 30 at a distance from the location where the toothed ring 240 of the coupling element 24 meshes with the inner toothed ring 303 of the roller element 300. The transmission of the radial pressing force, on the one hand, and the transmission of the torque, on the other hand, are therefore spatially separate from each other. Moreover, the pump head 30 here can be formed by a single, advantageously integrally formed roller element 300, of which the radial extent inside the depression 555 can be additionally maximized.

The invention claimed is:

1. A device for supplying and/or aspirating a fluid substance to or from a human or animal body, which device has
a drive unit with a drive;
an attachment part which is attachable to the drive unit and which has a peristaltic pump unit with a pump head, a hose guide, and a hose placed in the hose guide, wherein the pump head has several roller elements which serve for rolling on the hose in order thereby to convey the fluid substance through the hose; and
a coupling element which is coupled to the pump head and which serves to transmit a movement from the drive to the pump head when the attachment part is attached as intended to the drive unit,
wherein the pump head has a state in which the pump head is decoupled from the coupling element, and in which the roller elements are able to touch each other and apply no mechanical pressure or a comparatively low mechanical pressure to the hose, and in addition a state in which the pump head is coupled to the coupling element, and in which the roller elements are pressed by the coupling element against the hose with a comparatively high mechanical pressure,
wherein the roller elements, in the decoupled state, are movable freely and independently of each other within a range which is laterally limited by the hose placed in the hose guide,
wherein the coupling element has a first toothing area, and the roller elements each have a second toothing area engaging, in the coupled state, in the first toothing area in such a way that a movement of the coupling element is transmitted directly to the roller elements, and wherein the roller elements are each formed as a hollow wheel which has an outer toothed ring that forms the second toothing area and a radially outwardly directed surface, with the outer toothed ring being arranged radially inside of the radially outwardly directed surface.

2. The device according to claim 1, wherein the one or more roller elements each have a lateral play in the decoupled state.

3. The device according to claim 1, wherein the roller elements in the coupled state are each pressed against the hose by the coupling element in such a way that, by comparison with the decoupled state, the roller elements visibly deform.

4. The device according to claim 1, wherein the coupling element has a conically shaped portion.

5. The device according to claim 1, wherein the coupling element has a cylindrical portion which, in the coupled state, serves to press the roller elements against the hose.

6. The device according to claim 1, wherein the coupling element is a part of the drive unit.

7. The device according to claim 1, wherein the coupling element is a part of the attachment part.

8. The device according to claim 7, wherein the attachment part is a fluid container for collecting or making available a fluid.

9. The device according to claim 1, wherein the pump head is injection molded.

10. An attachment part of a device for supplying and/or aspirating a fluid substance to or from a human or animal body, having a peristaltic pump unit with a pump head, a hose guide, and a hose placed in the hose guide, wherein the pump head has several roller elements which serve for rolling on the hose in order thereby to convey the fluid substance through the hose, wherein the pump head is coupled to a coupling element which serves to transmit a movement from a drive to the pump head, wherein, in a state decoupled from the coupling element, the roller elements are able to touch each other and apply no mechanical pressure or a comparatively low mechanical pressure to the hose, but in a coupled state, the roller elements are coupled to the coupling element in such a way that the roller elements are pressed by the coupling element against the hose with a comparatively high mechanical pressure, and wherein the roller elements, in the decoupled state, are movable freely and independently of each other within a range which is laterally limited by the hose placed in the hose guide, wherein the roller elements each have a second toothing area, which is adapted to engage, in the coupled state, in a first toothing area of the coupling element in such a way that a movement of the coupling element is transmitted directly to the roller elements, and wherein the roller elements are each formed as a hollow wheel which has an outer toothed ring that forms the second toothing area and a radially outwardly directed surface, with the outer toothed ring being arranged radially inside of the radially outwardly directed surface.

\* \* \* \* \*

UNITED STATES PATENT AND TRADEMARK OFFICE
CERTIFICATE OF CORRECTION

PATENT NO. : 11,486,382 B2
APPLICATION NO. : 16/489992
DATED : November 1, 2022
INVENTOR(S) : Lukas Bannwart It is certified that error appears in the above-identified patent and that said Letters Patent is hereby corrected as shown below:

In the Claims

At Column 13, Lines 10-11, "the one or more" should be -- the --.

Signed and Sealed this
Second Day of May, 2023

Katherine Kelly Vidal
*Director of the United States Patent and Trademark Office*